United States Patent [19]

Nagpal et al.

[11] Patent Number: 5,776,687
[45] Date of Patent: Jul. 7, 1998

[54] RETINOID INDUCED GENE

[75] Inventors: Sunil Nagpal, Lake Forest; Daniel DiSepio, Corona del Mar; Roshantha A. Chandraratna, Mission Viejo, all of Calif.

[73] Assignee: Allergan, Irvine, Calif.

[21] Appl. No.: 808,303

[22] Filed: Feb. 28, 1997

[51] Int. Cl.⁶ .............................. C12Q 1/68; C12P 19/34; C07H 21/02; C07H 21/04

[52] U.S. Cl. ...................... 435/6; 435/91.2; 536/24.3; 536/24.33; 536/23.1; 424/9.1; 424/9.2

[58] Field of Search ................ 435/6, 91.2; 536/24.3, 536/24.33, 23.1; 424/9.1, 9.2

[56] References Cited

U.S. PATENT DOCUMENTS 5,648,334   7/1997   Davis et al. ........................ 514/12

OTHER PUBLICATIONS

WashU Merck EST Project (Genbank sequence listing), Genbank Accession No. W47350, 1995.

Ex Parte Anderson 30 USPQ2d, 1866–1870., 1994

*Primary Examiner*—W. Gary Jones
*Assistant Examiner*—Dianne Rees
*Attorney, Agent, or Firm*—Daniel E. Altman, Esq.; Carlos A. Fisher, Esq.

[57] ABSTRACT

A novel human cDNA, called TIG3 (Tazarotene Induced Gene 3), inducible by RAR-selective retinoids and structurally related to a known tumor suppressor gene. Methods of detecting the TIG3 polynucleotide.

17 Claims, No Drawings

RETINOID INDUCED GENE

FIELD OF THE INVENTION

The present invention relates generally to the field of inducible gene expression. More specifically, the invention relates to a retinoid-inducible polynucleotide and assays that detect expression of this polynucleotide.

BACKGROUND OF THE INVENTION

Retinoids, which are the compounds comprising vitamin A and its derivatives, play important roles in a variety of biological phenomena. More particularly, retinoids are important for vision, hematopoiesis, bone development and pattern formation during embryogenesis. Retinoids also exhibit antiproliferative activities in certain biological contexts.

Retinoids also have been used extensively as pharmaceutical agents for treating various malignant and non-malignant skin diseases. Malignant skin diseases therapeutically responsive to retinoids include squamous cell carcinoma, actinic keratoses, basal cell carcinoma and Kaposi's sarcoma. Additionally, retinoids are potentially useful as pharmacological agents for the treatment of various epithelial cancers (Peck and DiGiovanna, "Synthetic Retinoids in Dermatology" in *The Retinoids*, 2nd ed., pp 631-658 (1994); Boehm et al., *Exp. Opin. Invest. Drugs* 4:593 (1995); Nagpal and Chandraratna, *Curr. Pharm. Design* 2:295 (1996)). Examples of non-malignant skin diseases therapeutically responsive to retinoids include psoriasis and acne. In spite of the demonstrated utility of this class of pharmacological agents, the molecular basis of retinoid action in skin and various cancers is poorly understood.

Two families of nuclear receptors, called the retinoic acid (RA) receptors (RAR-α, -β and -γ) and the retinoid X receptors (RXR-α, -β and -γ), mediate pharmacological and physiological retinoid signalling (Chambon, *Sem. in Cell Biol.* 5:115 (1994); Mangelsdorf et al., "The Retinoid Receptors" in *The Retinoids*, 2nd ed., pp 319-349 (1994); Boehm et al., *Exp. Opin. Invest. Drugs* 4:593 (1995); Nagpal and Chandraratna, *Curr. Pharm. Design* 2:295 (1996)). RARs and RXRs, which belong to the superfamily of steroid/thyroid/vitamin $D_3$ nuclear receptors, readily heterodimerize in vitro (for references see, Nagpal and Chandraratna, *Curr. Pharm. Design* 2:295 (1996)) and function as heterodimers in vivo (Nagpal et al., *EMBO J.* 12:2349 (1993)). These receptors are ligand-dependent transcription factors which activate the expression of retinoid responsive genes by cooperative action of their activation functions. These activation functions are called AF-1, a ligand-independent activation function, and AF-2, a ligand-dependent activation function (Nagpal et al., *EMBO J.* 12:2349 (1993)).

The two families of retinoid receptors differ from each other with respect to the ligands that bind and activate the receptors. All-trans-RA (RA) binds and activates the RAR family of receptors. A different ligand, 9-cis-RA (9C-RA), binds and activates both the RARs and members of the retinoid X receptor (RXR) family. The retinoid called AGN 190168 (Tazarotene/ethyl 6-[2-(4,4) dimethyl-thiochroman-6-yl] ethynyl-nicotinate) is one example of an RAR-α/γ selective synthetic retinoid having therapeutic utility. More specifically, this synthetic retinoid can be administered topically to dramatically improve the symptoms associated with psoriasis.

Only a small number of retinoid-inducible gene products have been identified to date. Of these, the gene product encoding a cellular retinoic acid binding protein, called CRABP II, is the only marker known to be induced in vivo by RA in non-diseased skin (Elder et al., *J. Invest. Dermatol.* 100:356 (1993)). Interestingly, CRABP II expression was down-regulated by RA in submerged keratinocyte cultures (Elder and Cromie, *J. Toxicol—Cut. & Ocular Toxicol.* 12:173 (1993)) and was overexpressed in cells of tissues that exhibited a psoriatic phenotype (Didierjean et al., *Biochem. Biophys. Res. Comm.* 180:204 (1991)). Those having ordinary skill in the art will appreciate that psoriasis is a hyperproliferative and inflammatory condition of the skin (Krueger and Duvic, *J. Invest. Dermatol.* 102:14S (1994)) which clinically responds to retinoid treatment (Esgleyes-Ribot et al., *J. Am. Acad. Dermatol.* 30:581 (1994); Weinstein, *Brit. J. Dermatol.* 135(Suppl. 49):32 (1996)).

Two novel genes, called Tazarotene-induced gene 1 (TIG1) and Tazarotene-induced gene 2 (TIG2), were recently identified by virtue of their inducible expression in skin raft cultures treated with Tazarotene (Nagpal et al., *J. Invest. Dermatol.* 106:269 (1996); Nagpal et al., submitted (1997)). TIG1 was also shown to be induced by Tazarotene in foreskin keratinocyte and fibroblast cultures. Significantly, both TIG1 and TIG2 were induced in vivo by topical treatment of psoriatic lesions with Tazarotene.

Herein we disclose the discovery and utility of a novel retinoid-induced polynucleotide that is unrelated to either TIG1 or TIG2.

SUMMARY OF THE INVENTION

One aspect of the present invention regards an isolated polynucleotide that encodes a protein having the polypeptide sequence of SEQ ID NO:12. In a preferred embodiment the polynucleotide has the sequence of SEQ ID NO:11.

A second aspect of the invention regards a method of identifying a test compound for treatment of a hyperproliferative disorder of skin. According to the invented method, a negative control sample containing RNA isolated from an untreated control culture of cells derived from skin is first obtained. The cells of this control culture have not been treated with an inducer. Next, a test sample containing RNA isolated from a test culture of said cells derived from skin is obtained. Cells in this test culture will have been treated with the test compound. After the two samples of RNA have been obtained, the amount of Tazarotene Inducible Gene-3 (TIG3) RNA present in each of the samples is quantitated. The TIG3 RNA is an RNA having a polynucleotide sequence corresponding to the sequence of SEQ ID NO:11. Finally, the amount of TIG3 RNA in each of the samples is compared to determine if the amount of TIG3 RNA in the test sample is greater or lesser than the amount of TIG3 RNA in the negative control sample. A compound will be identified as a test compound for the treatment of the hyperproliferative disorder if the amount of TIG3 RNA in the test sample is greater than four-fold more than the amount of TIG3 RNA in the negative control sample. In a preferred embodiment, the step for quantitating TIG3 mRNA will involve hybridizing the negative control sample and the test sample with a labeled probe having a sufficient number of consecutive nucleotides complementary to the sequence of SEQ ID NO:11 to specifically hybridize with TIG3 mRNA under high stringency conditions (0.1× SSPE/1% SDS at 65° C.), and then quantitating the amount of hybridization between the probe and each of the samples. In another preferred embodiment, the negative control sample is derived from keratinocytes or fibroblasts. In yet other preferred embodiments, the TIG3 probe used in the procedures is labeled with a radioactive label and the amount of hybridized probe is quantitated by autoradiography. RNA contained in the negative control sample and RNA contained in the test sample can be immobilized to a solid support prior to the hybridizing step. In a different embodiment of the invented method, the step for quantitating the amount of TIG3 RNA present in negative control and test samples is accomplished by: (i) reverse transcribing mRNA present in each of the samples, wherein the product of reverse transcription has a polynucleotide sequence corresponding to a segment of the sequence given by SEQ ID NO:11, the product being TIG3 cDNA; (ii) amplifying specifically any TIG3 cDNA produced in step (i) by a polymerase chain reaction to result in the production of TIG3 amplification products; and (iii) quantitating the TIG3 amplification products produced when negative control and test samples are separately used as sources of RNA templates for the reverse transcribing step. In the practice of this method, the results of step (iii) can be normalized to the amount of a constitutively expressed mRNA present in both said negative control sample and said test sample. Preferred oligonucleotide primers useful for amplifying the TIG3 cDNA have the sequences of SEQ ID NO:13 and SEQ ID NO:14. In still yet another preferred embodiment of the invented method the quantitating step comprises a nuclease protection assay. More particularly, the nuclease protection assay can include: (a) hybridizing with nucleic acids in the negative control sample and the test sample a single stranded polynucleotide probe having a sequence complementary to a segment of the sequence of SEQ ID NO:11 linked to a contiguous stretch of nucleotides not complementary to the sequence of SEQ ID NO:11, where the complementary sequence is sufficient in length to hybridize specifically to TIG3 mRNA in an aqueous buffer made 80% formamide; (b) digesting products of hybridizing step (a) with a single-strand-specific nuclease; (c) separating products of digesting step (b) by electrophoresis; and (d) quantitating the amount of undigested probe remaining after digesting step (b) wherein the undigested probe quantitated has a length which corresponds to the sequence of said single-stranded polynucleotide probe which is complementary to the sequence of SEQ ID NO:11. In a particular embodiment, the single-strand-specific nuclease is S1 nuclease or RNase. In separate preferred embodiments of the invented method, the skin cells in the untreated control and in the culture treated with the test compound can be psoriatic skin cells, but alternatively may be non-psoriatic skin cells. In still yet another preferred embodiment of the invented method, the quantitating step comprises: (i) hybridizing with the negative control sample and the test sample a labeled DNA primer complementary to a segment of a polynucleotide having the sequence of SEQ ID NO:11 to result in a hybridized primer; (ii) extending the hybridized primer by the activity of a reverse transcriptase enzyme to produce cDNA; (iii) quantitating the amount of labeled cDNA produced in the extending step, wherein the cDNA quantitated has a length which corresponds to the number of nucleotides between the 5' end of said hybridized primer and the 5' terminus of the TIG3 mRNA. In a specific application of this latter embodiment, the labeled primer can be labeled at its 5"end.

A third aspect of the invention regards expression vectors for expressing a TIG3 polypeptide in a eukaryotic cell. These expression vectors include a polynucleotide which encodes the TIG3 polypeptide, where the TIG3 polypeptide has the amino acid sequence of SEQ ID NO:12, and a promoter operationally linked to this polynucleotide. In one embodiment, the TIG3 encoding polynucleotide has the sequence of SEQ ID NO:11, and the promoter is a human cytomegalovirus promoter.

DETAILED DESCRIPTION OF THE PREFERRED EMBODIMENT

Overview

Herein we disclose the sequence and utility of a novel polynucleotide that is induced in a wide variety of cell types by retinoids of the RAR subtype. Expression of this polynucleotide, identified below as "Tazarotene Induced Gene 3" (TIG3), was induced from a low basal level to a higher level in normal control keratinocytes in vitro and in biopsies of psoriatic plaques in vivo that had been treated with the anti-psoriatic retinoid called Tazarotene. Significantly, we have discovered that cell lines derived from human cancers and cancerous tumor cells present in several resected tissue samples both expressed the TIG3 mRNA at reduced levels compared to non-tumor cells. Moreover, cancer-derived cell lines that are growth inhibited by retinoids (i.e., T47D breast cancer cells) express TIG3 mRNA after retinoid treatment, but cell lines that are not growth inhibited (i.e., MCF7) do not express TIG3 mRNA in response to retinoid treatment. Importantly, the TIG3 polynucleotide and predicted polypeptide sequences were found to be related to those of a known tumor suppressor gene. These features of TIG3 gene expression provide a basis for developing nucleic acid and protein based assays for retinoid activity.

Introduction

As detailed below, we searched for novel retinoid-inducible gene sequences in order to obtain reagents useful as indicators of retinoid action, and to better understand the molecular mechanism of retinoid activity in skin. This search was directed particularly to the isolation of gene sequences induced in skin culture systems by the anti-psoriatic retinoid called Tazarotene (Esgleyes-Riboty et al., 1994; Weinstein, *Brit. J. Dermatol.* 135(Suppl. 49):32 (1996)). Since Tazarotene was known to be topically effective for the treatment of psoriasis, we reasoned that understanding its mechanism of action would provide insight into the molecular basis of retinoid action in the disease state.

Differential-display PCR (DD-PCR) procedures were used to identify Tazarotene-inducible polynucleotides. As a result of these procedures, we have now identified Tazarotene-induced gene 3 (TIG3), a novel gene product that is upregulated by Tazarotene in keratinocyte and skin raft cultures and in cells of biopsied psoriatic skin lesions that had been treated with Tazarotene. Thus, in addition to inducibility in vitro, TIG3 expression also was induced in vivo by topical treatment of psoriatic lesions with an RAR-selective retinoid. Assays for retinoid derivatives that induce the TIG3 mRNA provide a means for identifying compounds that can be further investigated as candidates for the treatment of a wide variety of retinoid responsive diseases.

Analysis of the TIG3 polynucleotide sequence revealed homology to the H-rev107 tumor-suppressor gene. This unexpected relationship initially suggested that TIG3 also had tumor suppressor or anti-proliferative activity.

Interestingly in view of its structural relatedness to the H-rev107 gene, the TIG3 mRNA was expressed in various normal tissues but not in cancerous cell lines representing these tissues, or in several primary tumors. Moreover, TIG3 was induced by Tazarotene in breast cancer cell lines that responded to the inhibitory effects of retinoids, but not in breast cancer cell lines that were refractory to retinoid mediated anti-proliferative activity. Taken together, these results suggested that TIG3 may be required for the normal growth control of cells in various tissues. These results also indicated that assays for detecting TIG3 mRNA inducibility in tumor cells treated with an RAR-selective retinoid such as Tazarotene could be adopted for use as a screening technique to identify tumor cells that were responsive to the growth inhibitory effects of retinoids.

One aspect of the present invention regards assays that can identify compounds having "bioactivity." As used herein, the term "bioactivity" refers to the ability of a chemical compound to affect an observable change in a biological system. In this context the synthetic retinoid Tazarotene is an example of a drug that exhibits bioactivity in assays encompassed by the present invention. In particular, Tazarotene stimulates expression of the novel gene, TIG3. Since this activity can be detected as increased expression of the TIG3 mRNA, Tazarotene is said to exhibit bioactivity. Drugs that fail to induce the TIG3 mRNA would be said to exhibit no bioactivity in this assay system.

In addition to nucleic acid-based assays for detecting TIG3 mRNA expression and induction, we contemplate immunological assays that employ anti-TIG3 antibodies as reagents for identifying bioactive retinoids. In this regard, we contemplate the production of anti-TIG3 antibodies for use as reagents in the detection of TIG3 protein. More specifically, we contemplate that all or part of the TIG3 cDNA disclosed herein can be operationally ligated to prokaryotic or eukaryotic expression or gene fusion vectors and introduced into living cells. The proteins encoded by these vectors can be used as immunogens to elicit the production of TIG3-specific antibodies. One advantage of using fusion proteins as immunogens derives from the fact that fusion proteins can be partly purified more easily than native proteins. Fusion proteins appropriate for the production of TIG3 immunogens can be any fusion protein familiar to one having ordinary skill in the art. Such fusion proteins can, for example, comprise glutathione S-transferase (GST) protein sequences as encoded by vectors that are available from Pharmacia (Piscataway, N.J.). Other vectors appropriate for the production of TIG3 immunogens can direct the expression of TIG3-protein A fusion proteins or fusion proteins having metal-binding domains or epitopes recognized by commercially available antibodies.

According to an alternative strategy for the production of anti-TIG3 antibodies, synthetic peptides predicted to represent antigenic regions of the TIG3 protein can be employed as immunogens. For example, these synthetic peptides can be coupled to carriers such as keyhole limpet hemocyanin (KLH) with MBS (Pierce, Rockford, Ill.) and used as immunogens for the production of anti-TIG3 antiserum. Antibodies produced in this fashion can be used to detect the TIG3 protein by cell staining, immunoprecipitation and Western blotting protocols. Anti-TIG3 antibodies can be used as reagents for detecting the induction of TIG3 proteins by retinoids that include Tazarotene, and other compounds having potential as therapeutics in the treatment of psoriasis and other retinoid responsive diseases.

Among the types of diseases contemplated as therapeutic targets of retinoids that induce TIG3 are: psoriasis, acne, dysplasias and cancers. The category of contemplated dysplasias includes precancerous lesions of the epithelial tissues such as oral leukoplakias, dysplasia of the cervix, larynx and bronchi. The category of contemplated cancers includes carcinomas of the skin, head and neck, cervix, uterus, breast and prostate. Synthetic retinoids may also be therapeutically effective for the treatment of atopic dermatitis, allergic rhinitis and asthma.

Finally, another aspect of the present invention relates to recombinant DNA constructs useful for expressing the TIG3 polypeptide in eukaryotic cells. Those having ordinary skill in the art will appreciate that recombinant DNA constructs of this sort generally are termed "expression vectors." Expression vectors of the invention are structurally related in that a polynucleotide encoding a polypeptide having the sequence of SEQ ID NO:12 is operationally linked downstream of a promoter element. A promoter element is a DNA element capable of directing transcription in the nucleus of a cell. By operationally linked it is meant that a polynucleotide translatable as the polypeptide of SEQ ID NO:12 is transcribed from the promoter of the expression vector. This is distinguished from a case wherein an antisense transcript is produced that cannot be translated into a polypeptide having the sequence of SEQ ID NO:12. An exemplary polynucleotide encoding the TIG3 polypeptide has the sequence of SEQ ID NO:11. Exemplary promoters useful in connection with the invention include: promoters derived from viruses and promoters derived from eukaryotic genomes. Synthetic promoters also are contemplated for use in connection with the invention. Promoters falling under the category of viral promoters include: retroviral promoters, adenoviral promoters, adeno-associated virus promoters and herpes virus promoters. A human cytomegalovirus (CMV) promoter is specifically contemplated for operational linkage to a polynucleotide encoding the polypeptide of SEQ ID NO:12. In a particular embodiment described herein, an expression vector comprising the human cytomegalovirus promoter operationally linked to a polynucleotide having the sequence of SEQ ID NO:11 was created to illustrate the construction of a TIG3 expression vector.

Definitions

As used herein, a "hyperproliferative disorder" is a mild or severe pathological condition resulting from excessive cell proliferation. As illustrative examples, psoriasis is a condition associated with keratinocyte hyperproliferation while a tumor is a condition characterized by hyperproliferation of a clonal population of cells. A specific example of a tumor would be a carcinoma, which is a malignant tumor of the epithelium.

As used herein, the phrase "treating a hyperproliferative disorder" is intended to refer to a therapeutic process for improving the symptoms associated with a hyperproliferative disorder as would be understood by one having ordinary skill in the art. For example, effectively treating the hyperproliferative disorder called psoriasis would result in an improvement of the scaling and inflammation associated with the disease. In general, treating a hyperproliferative disorder in the context of the invention is intended to refer to reducing the rate of cell division in cells that are at the root cause of the disorder.

Although other materials and methods similar or equivalent to those described herein can be used in the practice or testing of the present invention, the preferred methods and materials are now described. General references for methods that can be used to perform the various nucleic acid manipulations and procedures described herein can be found in *Molecular Cloning: A Laboratory Manual* (Sambrook et al., eds. Cold Spring Harbor Lab Publ. 1989) and *Current Protocols in Molecular Biology* (Ausubel et al., eds., Greene Publishing Associates and Wiley-Interscience 1987). The disclosures contained in these references are hereby incorporated by reference. A description of the experiments and results that led to the creation of the present invention follows.

A variety of skin-derived cells were used in the development and practice of the present invention. The cells employed in these procedures served as sources of RNA used as templates for polymerase chain reaction (PCR) amplification procedures and for the analysis of retinoid-regulated gene expression using a variety of techniques, including blot hybridization and PCR based detection protocols. Unless specified otherwise, all cell and tissue samples used in the experimental procedures described herein were obtained from commercial sources. Primary cultures of human foreskin keratinocytes and fibroblasts were purchased from Clonetics (San Diego, Calif.). Normal skin raft cultures (model ZK 1300), which are three-dimensional human skin-like tissues, were purchased from Advanced Tissue Sciences (La Jolla, Calif.). While commercial sources of cells and tissues are preferred for reasons of convenience, primary cultures of human cells prepared according to the method of the following Example can be used with equally good results.

Example 1 describes the methods used to obtain non-transformed human keratinocytes and fibroblasts.

Example 1

Establishment of Primary Cell Cultures of Human Keratinocytes and Fibroblasts

Fresh human foreskins were washed in ethanol (70%) for 10 seconds followed by two washings in keratinocyte growth medium (KGM) purchased from Clonetics (San Diego, Calif.). Tissue samples were cut into small pieces (4 mm diameter) and incubated with trypsin (0.05% GIBCO-BRL, Grand Island, N.Y.) for 24 hours at 4° C. After digestion, the epidermis that contained keratinocytes was removed and dissociated into a cell suspension using sterile forceps. Keratinocytes were pelleted at 1000×g in a Beckman model TJ-6 centrifuge for 6 minutes at 4° C. The resulting cell pellet was then resuspended in KGM and filtered through a 100 micron nylon mesh membrane from Tetko, Inc. (New York, N.Y.). The filtrate, which contained keratinocytes, was cultured in a T75 tissue culture flask with 20 ml of KGM containing 10% fetal bovine serum (FBS). After three days the culture medium was replaced with KGM that did not contain FBS. Keratinocytes were maintained in serum-free media and split at 80% confluence for four passages prior to retinoid treatment.

Fibroblasts were isolated by first cutting the remaining dermis from the foreskins into small pieces using a scalpel, and then incubating with Hanks' buffer containing collagenase (0.1% for 1 hour at 37° C.). The digest was filtered through a nylon mesh and centrifuged as before. Fibroblasts were resuspended in 20 ml DMEM containing 10% FBS in a T75 tissue culture flask. Cells were maintained in DMEM with FBS, split at 80% confluence and used for procedures involving treatment with retinoids after 2–3 passages.

In addition to the keratinocyte cultures prepared as described above, three-dimensional reconstructed skin raft cultures were also used in procedures involving retinoid induction and RNA isolation. Normal skin raft cultures, which are alternatively called "organotypic" or "skin equivalent" cultures, can be obtained commercially. The normal skin raft cultures employed in the procedures described herein were purchased from Advanced Tissue Sciences (La Jolla, Calif.).

The structural relationships among the cellular and acellular components comprising these skin raft cultures advantageously reproduce some of the complex features which characterize skin. In particular, skin raft cultures represent three-dimensional biological models having dermal, epidermal and corneal layers. In the production of these cultures, neonatal fibroblasts were seeded onto an inert nylon mesh and grown into a dermal tissue. Keratinocytes seeded atop this dermal layer gave rise to an epidermis.

In addition to normal skin raft cultures, we also employed skin raft cultures prepared from psoriatic fibroblasts and normal human keratinocytes. These "psoriatic skin raft cultures" were perturbed in their epidermal morphology when compared to their normal counterparts. Thus, these cultures advantageously retained at least some of the pathologic features which characterized the condition of the fibroblast donor.

The following Example details the method used to isolate the novel retinoid inducible TIG3 polynucleotide. The DD-PCR technique employed in this procedure involved separately amplifying subsets of the population of transcripts expressed by mock-treated and Tazarotene-induced human keratinocytes. Side-by-side electrophoretic separation and visualization of the amplified cDNAs facilitated comparison of the polynucleotides represented in the two RNA populations. The presence of an amplification product in the lane representing RNA isolated from the induced cell, and the absence of a corresponding band in the lane representing RNA isolated from mock-treated cells identified a polynucleotide representing a retinoid-induced transcript. As described below, the inducible transcript identified in the following Example unexpectedly was found to be structurally similar to a known tumor suppressor gene.

Example 2 describes the methods used to identify and isolate a polynucleotide representing a retinoid-inducible gene product.

EXAMPLE 2

Isolation of a Retinoid Responsive Polynucleotide

Parallel cultures of primary human keratinocytes prepared according to the method of Example 1 were mock treated with ethanol vehicle alone or induced with 1 µM Tazarotene (AGN 190168) for three days. At the end of the treatment period total RNA was isolated according to standard laboratory methods and used as a template for 40 cycles of PCR essentially according to the method of Liang et al., (*Science* 257:967 (1992)). Reagents used to conduct the DD-PCR procedure included a HYROGLIPH kit purchased from Genomyx, Inc. , (Foster City, Calif.) and EXPAND polymerase purchased from Boehringer Mannheim (Indianapolis, Ind.). We realized that use of a high cycle number was likely to introduce at lease some replication errors into the sequence of the amplified polynucleotides, but reasoned that the presence of these sequence errors would not diminish our ability to identify inducible transcripts. According to a standard protocol that will be familiar to those having ordinary skill in the art, paired combinations of pooled oligonucleotides were used as primers to amplify cDNAs subsequent to a reverse transcription step. Amplification reactions also included [$^{33}$P]-dATP so that all reaction products were radiolabeled uniformly. Amplified cDNAs were electrophoretically separated on a long-range 4.5% polyacrylamide gel for 16 hours, and the resulting gel exposed to X-ray film to visualize the amplification products.

Autoradiographic results revealed that an amplification product having a length of approximately 0.6 kb was detected only in one of the gel lanes that had been loaded with products of a reaction primed with RNA isolated from Tazarotene-induced keratinocytes. No equivalent band was detected in the lane representing products of a reaction primed with RNA isolated from mock-treated cells. This difference indicated that the 0.6 kb amplification product represented an mRNA transcript that was induced in keratinocytes by Tazarotene, and that had a length of at least 0.6 kb.

Inducibility of the mRNA corresponding to the 0.6 kb amplification product was confirmed by Northern analysis of RNA isolated from mock-treated and Tazarotene-induced keratinocytes. The 0.6 kb cDNA fragment was excised from the gel and re-amplified in a PCR procedure using the gel-isolated cDNA fragment as a template, the combination of PCR primers that had been employed to amplify the 0.6 kb polynucleotide originally, and EXPAND polymerase (Boehringer Mannheim; Indianapolis, Ind.) in a standard PCR amplification procedure. The resulting amplification product was labeled with [$^{32}$P]-dCTP (Amersham; Arlington Heights, Ill.) by nick translation and then used to probe a Northern blot having one lane each of total RNA isolated from mock-treated and Tazarotene-induced keratinocytes, with 15 µg of RNA in each lane. Even though the amplification product may have included replication errors sustained as the result of a high number of PCR cycles, these few errors were not likely to compromise the utility of the amplification product as a hybridization probe. Following hybridization with the labeled probe at 60° C. for 2 hours in QUICKHYB hybridization solution (Stratagene; La Jolla, Calif.), the Northern membrane was washed under high stringency conditions of 0.1×SSC and 1% SDS at 65° C. for 15 minutes and then exposed to X-ray film.

Northern blotting results indicated that the labeled 0.6 kb probe hybridized specifically to a single 0.8–0.9 kb transcript present in the RNA population isolated from Tazarotene induced keratinocytes. A weakly detectable signal was observed in the lane representing mock-treated keratinocyte RNA while a stronger signal was observed in the lane representing Tazarotene-induced RNA. Quantitation of the band intensities on the X-ray film indicated that the mRNA detected by the 0.6 kb probe was increased by at least 4 fold in human keratinocytes following induction with Tazarotene. This result proved that a radiolabeled form of the 0.6 kb amplification product described above was useful for specifically detecting a retinoid-inducible mRNA. Specificity of the hybridization was demonstrated by virtue of the unique interaction between the 0.6 kb probe and the single species of polynucleotide immobilized on the Northern blot and visualized as a single band on the autoradiograph. In view of the utility of the amplified polynucleotide as a reagent useful for detecting retinoid-induced gene expression, the amplified polynucleotide was ligated into a plasmid vector and cloned as a step toward further characterizing the structure and function of the corresponding gene product.

Notably, the fact that a unique Tazarotene induced mRNA species was detected in the Northern blotting procedure described above confirmed that other hybridization protocols, for example based on dot or slot blotting techniques, would also be useful for detecting expression of the TIG3 mRNA.

The 0.6 kb amplification product representing a portion of a 0.8–0.9 kb Tazarotene-inducible transcript was ligated into a plasmid vector and cloned according to standard laboratory procedures. More specifically, an aliquot of the amplification reaction that contained the 0.6 kb fragment was combined with the linear form of the pCRII TA CLONING vector that had been purchased from Invitrogen (San Diego, Calif.), ligated, transformed into competent E. coli host cells and selected on plates containing ampicillin. Several well isolated colonies picked from one plate represented clones harboring copies of the 0.6 kb fragment as inserts. One of the clones was called pTA-TIG3.

Both strands of the inserts contained in six independent plasmid isolates, pTA-TIG3 being among these isolates, were sequenced in standard dideoxy chain termination protocols using SP6 and T7 sequencing primers. The polynucleotide sequence of the cDNA insert contained in plasmid pTA-TIG3 is presented as SEQ ID NO:1. A consensus polynucleotide sequence of the 0.6 kb fragment was deduced from alignment and comparison of the sequences of the six different clonal isolates and is presented as SEQ ID NO:2. Analysis of this consensus sequence revealed the presence of a poly(A) addition signal sequence (AATAAA) located 23 nucleotides upstream of a poly(A) tail at the 3' end of the polynucleotide molecule. In aggregate, these results indicated that the cloned 0.6 kb amplification product represented a partial cDNA that was missing polynucleotide sequence information at the 5' end of the molecule, but was otherwise complete at its 3' end. The predicted polypeptide sequence encoded by the polynucleotide of SEQ ID NO:2 is presented as SEQ ID NO:3.

A preliminary homology search of nucleic acid databases indicated that the polynucleotide sequence of the cloned 0.6 kb cDNA fragment was related to the sequence encoding the H-rev107 tumor-suppressor gene. Since the newly cloned polynucleotide may have encoded a protein having tumor suppressor activity, and in view of the fact that the polynucleotide was missing sequence information at its 5' end, we carried out procedures to isolate a polynucleotide representing the missing upstream sequence that was required to reconstruct the sequence of the full length cDNA.

A standard PCR protocol for the amplification of 5' ends of cDNA was used to obtain polynucleotide sequence information present in the TIG3 mRNA, but absent from the partial cDNA clone having the polynucleotide sequence identified herein as SEQ ID NO:2. A first primer having the sequence 5'-TTCACCTCTGCACTGTTGCTC-3' (SEQ ID NO:4), and corresponding to a region within the coding sequence of the cloned DNA insert of plasmid pTA-TIG3, and an SP6 primer were used to specifically PCR amplify the 5' end of TIG3 from a cDNA library containing total cDNA prepared from Tazarotene-treated skin raft cultures. The cDNA library used for this procedure had been constructed in the plasmid vector, pSPORT2 (Gibco-BRL, Gaithersburg, Md.). The SP6 primer used for this procedure had the polynucleotide sequence 5'-ATTTAGGTGACACTATAGAAGAGC-3' (SEQ ID NO:5). A polynucleotide of approximately 0.3 kb in length was amplified, cloned and sequenced, also according to standard procedures. The 5' TIG3 polynucleotide sequence of this amplification product, presented as SEQ ID NO:6, contained an ATG translation initiation codon and untranslated sequence upstream of the coding region. Alignment and combination of the polynucleotide sequences of SEQ ID NO:2 and SEQ ID NO:6 resulted in a polynucleotide sequence representing the full length TIG3 cDNA, presented here as SEQ ID NO:7. The full length TIG3 polypeptide sequence is presented as SEQ ID NO:8.

Example 3 describes the method used to obtain a single polynucleotide corresponding to the cDNA fragments represented by the 0.6 kb cDNA fragment and the 5' PCR product, and that contained a complete open reading frame. The oligonucleotide primers used in this procedure were derived from the upstream sequence of the 5' PCR amplification product and the downstream sequence of the 0.6 kb amplification product that included a region representing the 3' end of the transcript.

EXAMPLE 3

Isolation of a Polynucleotide Containing a Complete Open Reading Frame

First strand cDNA was synthesized using total RNA isolated from Tazarotene-induced keratinocytes as a template and oligo-d(T)$_{16}$ as a primer in a standard reverse transcription reaction. Reagents used for synthesizing cDNA were purchased as a kit from Perkin-Elmer (Norwalk, Conn.) This first strand cDNA then served as a template for a PCR amplification using Pfu DNA polymerase (Stratagene; La Jolla, Calif.) and primers having the sequences of 5'-TTGGATCCTGTGGCTGCTTCAGG-CTGTTGC-3' (SEQ ID NO:9) and 5'-TCAAGCTTCCACCATGGCTTCGCCACACCAAGA-GCCCA-3' (SEQ ID NO:10). This second primer contained a Hind III restriction cleavage site (AAGCTT) and a Kozak consensus sequence (CCACC) to ensure efficient translation of an mRNA transcript generated from the amplification product. Those having ordinary skill in the art will appreciate that the Pfu DNA polymerase employed in our procedures is a thermostable polymerase having proofreading activity. Pfu is a high fidelity polymerase with an error rate substantially lower than the error rate of Taq polymerase. The amplification product resulting from our procedures had a length of approximately 0.8 kb as judged by agarose gel electrophoresis and ethidium bromide staining, and contained the TIG3 polynucleotide sequence presented as SEQ ID NO:11. This amplification product was cleaved at the primer-derived restriction endonuclease cleavage sites using Hind III and Bam HI, and samples of the digested DNA ligated into the pcDNA3 plasmid expression vector (Invitrogen; San Diego, Calif.) that had been linearized using Hind III and Bam HI restriction endonucleases. The cDNA insert orientation was such that transcripts expressed from the plasmid-borne eukaryotic promoter would be translated into a polypeptide having the sequence of SEQ ID NO:12. The pcDNA3-based expression plasmid containing the cDNA insert was called pc-TIG3.

Example 4 describes the nucleic acid and protein sequence analysis used to assess novelty and possible function of the Tazarotene inducible gene product isolated according to the methods described above.

EXAMPLE 4

Analysis of the Predicted Protein Encoded by the TIG3 Polynucleotide Sequence The 736 bp long TIG3 cDNA contained an open reading frame extending from nucleotides 30–521 and encoded a putative protein of 164 amino acids in length. Computer-assisted homology searches of nucleic acid (Genbank and EMBL) and protein (Swiss-Prot) databases failed to identify any known DNA or protein sequence that was identical to the TIG3 nucleic acid or predicted protein sequence. However, this analysis revealed significant homology between the TIG3 clone and a rat and a human cDNA and protein (RNHrev107 and H-rev107, respectively). The predicted protein encoded by the TIG3 polynucleotide contained a potential hydrophobic domain between amino acids 133–151, a putative cAMP phosphorylation site between amino acids 160–163, a protein kinase-C (PKC) phosphorylation site between amino acids 95–97, and a casein kinase II (CK2) phosphorylation site between amino acids 95–98. The hydropathic profile of the TIG3 polypeptide resembled the hydropathic profile of H-rev 107. Conservation of the large hydrophobic region in the hydropathic profiles of the TIG3 and H-rev107 polypeptides, together with the fact that H-rev107 is known to be a membrane-associated protein, strongly suggested that TIG3 was also a membrane-associated or transmembrane protein. Given these interesting structural features of the TIG3 cDNA clone, we proceeded to further investigate the nature of retinoid inducibility of the TIG3 mRNA.

Example 5 describes the methods used to demonstrate that the TIG3 mRNA was induced in skin raft cultures selectively by RAR-specific retinoids.

EXAMPLE 5

Induction of TIG3 mRNA by RAR-Specific Retinoids

After demonstrating that TIG3 was induced by Tazarotene in primary keratinocyte monolayer cultures, we next investigated retinoid inducible TIG3 mRNA expression in other skin-derived cell culture systems. More particularly, the specificity of the retinoid receptor(s) participating in the signal transduction pathway leading to TIG3 mRNA induction was determined using a human normal skin raft culture system. RNA samples isolated from normal skin rafts that had been treated with vehicle alone or stimulated with a variety of retinoid agonists were assayed for TIG3 mRNA induction according to the Northern blotting method described above. More specifically, human normal skin rafts were treated for 5 days with either the RAR agonist Tazarotene, or RXR agonists AGN 193127 or AGN 193193. Retinoids were used at final concentrations of 1 µM. Total RNA isolated from the treated skin rafts was Northern blotted, probed with [$^{32}$P]-labeled PCR amplification product representing the TIG3 coding region (SEQ ID NO:11), washed under high stringency conditions of 0.1×SSC and 1% SDS at 65° C. for 15 minutes and then exposed to X-ray film to detect TIG3 mRNA transcripts.

Northern blotting results indicated that only the RAR agonist induced TIG3 mRNA expression. More specifically, we observed that TIG3 mRNA was induced at least 4 fold by treatment of normal skin raft cultures with Tazarotene. Expression was undetectable by Northern analysis in the RNA samples isolated from skin raft cultures that had been treated with vehicle alone or with one of the two RXR specific compounds. These findings provided strong evidence that TIG3 mRNA induction was mediated through an RAR-specific signal transduction pathway.

In a related procedure, total RNA that had been isolated from psoriatic skin raft cultures treated with vehicle, Tazarotene, or the free acid of Tazarotene at a concentration of 1 µM for 5 days, was Northern blotted and probed with a labeled TIG3 polynucleotide probe corresponding to the 0.6 kb insert in the pTA-TIG3 plasmid. Expression of the TIG3 mRNA was detected in the Tazarotene treated lane of the Northern blot, with higher expression being detected in the sample isolated from the skin raft culture that had been treated with the free acid of Tazarotene. Quantitative analysis of the autoradiograph of the Northern blot indicated that the TIG3 mRNA was induced at least 4 fold in psoriatic skin raft cultures when assayed by Northern blotting using a TIG3 polynucleotide probe and high stringency wash conditions of 0.1×SSC and 1% SDS at 65° C. for 15 minutes.

A PCR-based assay was used to detect TIG3 mRNA induction as an alternative approach for detecting retinoid activity. The extraordinary sensitivity of the PCR technique results from the fact that the quantity of a polynucleotide sequence can be amplified more than a million fold by repetitive cycles of DNA synthesis. By selecting a set of primers that can be used to amplify a second polynucleotide sequence that corresponds to a constitutively expressed mRNA, results effectively can be normalized between two different reactions. This normalization allows for a relative quantitation of the amount of starting material present in different samples. In the procedure described below, two oligonucleotide primers that could specifically amplify the TIG3 polynucleotide present in pooled RNA from patient biopsies were synthesized for use in RT-PCR protocols. Other primer sets based on the TIG3 cDNA sequence and selected using standard criteria readily appreciated by those of ordinary skill in the art can also be used to detect TIG3 mRNA expression. Indeed, any oligonucleotide primer set that can be used to uniquely amplify a segment of the TIG3 cDNA in a PCR procedure are anticipated for use in assays for detecting TIG3 mRNA induction, for example by retinoids. Additionally, the assay can be modified by substituting skin-derived fibroblasts or normal or psoriatic skin raft cultures or keratinocytes for the biopsy samples described below.

Example 6 describes the method that was used to detect TIG3 mRNA induction in biopsy samples from patients treated by topical application of Tazarotene.

EXAMPLE 6

In Vivo Induction of TIG3 mRNA in Psoriatic Lesions by Tazarotene

Retinoid inducibility of the TIG3 mRNA in vivo was verified using a PCR based assay. A pair of oligonucleotides having sequences 5'-GCGACAGCCTGAAGCAGC-3' (SEQ ID NO:13) and 5'-TTATTGATCCTTCAGTCTTG-3' (SEQ ID NO:14) were prepared for use as primers to amplify a portion of the 3' end of the TIG3 polynucleotide. Oligonucleotide primers for amplifying glyceraldehyde phosphate dehydrogenase (GAPDH) transcripts as a normalization control were purchased from Stratagene, Inc. , (La Jolla, Calif.) and used according to manufacturer's instructions.

Patients (n=20) having long-standing bilateral plaque psoriasis were treated twice daily with vehicle or 0.1% Tazarotene gel in a clinical study for up to 8 weeks. Punch biopsies were taken from 18 patients after 2 weeks of treatment and patients were assessed for their clinical response to the drug after 8 weeks. Total pooled RNA from 15 responders (patients with ≧40% decrease in total clinical score at day 56) was used in standard RT-PCR reactions to amplify the TIG3 and GAPDH transcripts. After oligo-dT primed reverse transcription of the mRNA in the samples, PCR amplification was conducted using either TIG3 or GAPDH primers. Aliquots of the reaction (10 µl) were removed after each cycle beginning at cycle 20. Reaction products were visualized by agarose gel electrophoresis and ethidium bromide staining.

Results indicated that the TIG3 mRNA was induced in biopsy samples of Tazarotene treated psoriatic plaques. More specifically, a 190 bp TIG3 amplification product was detected after only 24 cycles of PCR when RNA isolated from Tazarotene treated plaques served as a template in the reaction. In contrast, the 190 bp amplification product was not detected until 27 cycles in reactions that employed RNA isolated from vehicle-treated control plaques. This result proved that TIG3 mRNA expression was induced in psoriatic plaques following treatment with Tazarotene. Significantly, the expression of GAPDH in the samples was unaffected by Tazarotene treatment as judged by detection of the GAPDH amplification product after 24 cycles of PCR in both the control and Tazarotene treated biopsies.

Example 7 describes the procedures used to demonstrate that the TIG3 mRNA was constitutively expressed in a variety of normal tissues but not in cultured cells derived from malignant tumors.

EXAMPLE 7

TIG3 mRNA is Constitutively Expressed in Normal Tissues but Not in Cell Lines Derived from Human Cancers Multiple-tissue Northern blots purchased from Clonetech Laboratories, Inc. (Palo Alto, Calif.) were probed with a radiolabeled TIG3 polynucleotide probe according to the method of Example 2 to investigate constitutive expression in various normal tissues. In a separate procedure, Northern blotted RNA samples isolated from various cell lines derived from human cancers were also probed for TIG3 transcripts. TIG3 mRNA expression levels were then compared to expression levels measured by a similar procedure in non-cancerous tissues. More specifically, RNA samples used to prepare the Northern blot representing cancer-derived cell lines were isolated from A549 lung carcinoma cells, SW480 colorectal adenoma cells, HL60 cells and K562 cells.

Results indicated that the TIG3 mRNA was easily detected in lanes of the blot representing RNA isolated from normal human lung, liver, kidney, spleen, thymus, prostate, ovary, small intestine, colon and peripheral blood leukocytes. Expression was not detected in heart, brain, placenta, smooth muscle, pancreas or testis. This result indicated that TIG3 mRNA was constitutively expressed at an easily detectable basal level in a tissue-restricted fashion. In contrast to the high levels of TIG3 mRNA expression detected in normal lung, colon, and peripheral leukocytes, little or no TIG3 mRNA expression was detected in RNA samples isolated from A549 lung carcinoma cells, SW480 colorectal adenoma cells, HL60 promyelocytic leukemia or K562 chronic myelocytic leukemia.

Example 8 describes the procedures used to demonstrate that TIG3 transcripts were constitutively expressed in non-tumor cells and expressed at a substantially lower level in tumor cells. As disclosed below, a variety of non-tumor and cancerous tissue samples isolated from humans were analyzed for TIG3 mRNA expression levels to assess differences between the level of expression in malignant and non-malignant regions of a single surgically resected sample.

EXAMPLE 8

Constitutive Expression of TIG3 mRNA Distinguishes Normal Tissue and Primary Tumor Tissue Total RNA blots containing RNA isolated from resected tumors and adjacent healthy, non-tumor tissue were purchased from Invitrogen (San Diego, Calif.). The blots were probed according to standard procedures described above using radiolabeled TIG3 and GAPDH probes. The probe used for detecting TIG3 mRNA in this procedure corresponded to the 0.6 kb insert of plasmid pTA-TIG3. The probe was prepared using a standard PCR amplification protocol in the presence of radiolabeled nucleotides. Tumor samples included: brain, kidney, liver, lung, esophagus, stomach, colon, rectum, bladder, breast, uterus, fallopian, ovarian, thyroid, adrenal, parotid and lymphoma.

Results indicated that TIG3 was constitutively expressed in many normal tissues. More specifically, the TIG3 mRNA was constitutively expressed in kidney, ureter, rectum, uterus, and lymph node. However, TIG3 mRNA expression was either reduced or undetectable in the cancerous counterparts of these tissues. Some of the tissues (colon, stomach, breast, liver, fallopian tube, ovary, thyroid and parotid) did constitutively express TIG3 but did not show any significant differences in the expression of TIG3 when compared to the cancerous region of the tissue sample.

The decreased expression of TIG3 mRNA in some primary tumors strongly suggested an anti-proliferative or growth regulatory role for TIG3. Further, it should be noted that TIG3 expression may not be aberrant in all tumors, a situation analogous to other tumor suppressor genes such as p53 and BRCA1, which are mutated in some, but not all tumors.

Additionally, while TIG3 mRNA was expressed in primary keratinocytes that served as a normal control, neither constitutive basal level expression nor retinoid inducible expression could be detected in HaCaT cells that represented transformed keratinocytes. This finding supported the conclusion that the TIG3 gene product possessed antiproliferative activity.

In order to further explore the pattern of basal expression and retinoid inducibility of the TIG3 mRNA in the context of hyperproliferative disorders, we turned to an in vitro system of breast cancer cell lines. Those having ordinary skill in the art will appreciate that some retinoids are known to inhibit the proliferation of a subset of breast cancer cell lines in vitro (Rubin et al. Cancer Res. 54:6549 (1994)). We reasoned that if the TIG3 polynucleotide encoded a protein having anti-proliferative activity, then the TIG3 mRNA might be induced by retinoids in cells that were growth-inhibited by retinoids but not in cells that were resistant to the growth-inhibitory effects of retinoids. T47D and ZR75-1 are examples of retinoid-sensitive breast cancer cell lines that are proliferation-inhibited by Tazarotene or the RAR-selective retinoid called TTNPB (AGN 191183) in a dose-dependent manner. MCF-7 and MDA-MB-231 are examples of breast cancer cell lines that are resistant to the antiproliferative activities of Tazarotene and TTNPB.

Example 9 describes the method used to demonstrate that the TIG3 mRNA was selectively induced only in the cancer-derived cell lines that were growth-inhibited by exposure to RAR-selective retinoids.

EXAMPLE 9

Tazarotene Induces TIG3 mRNA Expression in Retinoid-Responsive Breast Cancer Cells but not in Retinoid Non-Responsive Breast Cancer Cells The T47D, ZR75-1, MCF-7 and MDA-MB-231 cell lines were propagated in culture according to standard procedures familiar to those having ordinary skill in the art. Samples of each culture were split two ways, with one aliquot from each culture being treated with vehicle alone as a control. The second aliquot from each culture was treated with Tazarotene at a concentration of 0.1 µM for a period of three days. Total RNA isolated from each of the vehicle control and Tazarotene-treated cultures was Northern blotted and probed with radiolabeled TIG3 and GAPDH probes according to the protocols described above. More particularly, the probe used for detecting TIG3 mRNA in this procedure corresponded to the 0.6 kb insert of plasmid pTA-TIG3. The probe was prepared using a standard PCR amplification protocol in the presence of radiolabeled nucleotides. Northern blotting results indicated that Tazarotene-induced TIG3 mRNA expression was detected only in T47D and ZR75-1 cells, but not in MCF-7 or MDA-MB-231 cells.

The experimental results presented to this point indicated that assays for TIG3 mRNA induction would be useful for identifying candidate agents for treating hyperproliferative disorders. Evidence supporting this conclusion included the structural similarity between the TIG3 and H-rev107 polynucleotides, the fact that the H-rev107 polynucleotide encoded a protein having antiproliferative activity, and the fact that the anti-psoriatic retinoid Tazarotene induced TIG3 mRNA expression in psoriatic plaques that were characterized by keratinocyte hyperproliferation. Accordingly, it would be useful to exploit TIG3 mRNA inducibility in drug screening assays.

The following Example illustrates how blot hybridization protocols can be used to identify compounds having bioactivity similar to Tazarotene. In this procedure, Tazarotene was used as a positive control for compounds that induce TIG3 expression. Mock-induction of the same cultured cell type was used as the negative control in this procedure. Test compounds identified as inducers of TIG3 mRNA according to the following procedure are regarded as candidates for the treatment of hyperproliferative disorders.

In the practice of the method described below, determination of retinoid bioactivity is based on the ability of test compounds to induce TIG3 mRNA expression above the level of basal expression detected in RNA samples isolated from untreated control cells. Accordingly, if an RNA sample isolated from cells treated with a test compound does not contain proportionately more TIG3 mRNA than a sample isolated from untreated control cells, then that test compound will be judged to have no bioactivity. Thus, RNA samples isolated from untreated control cells or cells treated with a compound that does not induce TIG3 mRNA expression serves as a baseline for measuring inducible expression. Compounds having bioactivity similar to that of Tazarotene are identified by comparing expression of TIG3 mRNA in cells treated with test compounds and cells treated with Tazarotene as a positive control for TIG3 mRNA induction.

As described below, the invented assay has been used to prove that at least one RAR-specific retinoid, in addition to Tazarotene, induced TIG3 mRNA expression in psoriatic skin raft cultures. Accordingly, this RAR-specific retinoid is a candidate agent for treating hyperproliferative disorders according to the method of the present invention. In contrast, compounds that do not substantially induce TIG3 mRNA expression above the basal level observed in untreated cells would not be considered for further evaluation as an agent for treating hyperproliferative disorders according to the invented method.

Example 10 describes a blot hybridization assay for identifying compounds that induce TIG3 mRNA expression in psoriatic skin raft cultures. Skin-derived keratinocytes, fibroblasts and normal skin raft cultures can be substituted for the psoriatic skin raft cultures of the following procedure with equally good results.

EXAMPLE 10

Hybridization Assay for Induction of the TIG3 mRNA by Retinoids

Psoriatic skin raft cultures were propagated under standard conditions. Parallel cultures were mock-treated or induced with 1 µM concentrations of the retinoid to be tested for bioactivity. A mock-treated culture was used as a negative control to establish basal level expression of TIG3 mRNA. The RAR-specific ligand Tazarotene was used as a positive control for TIG3 induction. The RAR-specific ligand, AGN 190299 (6-[2-(4,4) dimethyl-thiochroman-6-yl] ethynyl-nicotinic acid), was used as a test compound in this exemplary procedure. All cultures were induced for four days after which time total RNA was isolated by standard laboratory procedures. RNA (10 µg) from each of the three samples was separated by electrophoresis on 1% agarose, 1.1M formaldehyde gels, transferred to nytran membranes and probed with [$^{32}$P]-labeled TIG3 cDNA probe corresponding to the 0.6 kb insert of plasmid pTA-TIG3. The probe was prepared using a standard PCR amplification protocol in the presence of radiolabeled nucleotides. The same blots were subsequently stripped and re-probed with [$^{32}$P]-labeled GAPDH cDNA probes. Blots were hybridized in QUICKHYB (Stratagene; La Jolla, Calif.) according to manufacturer's instructions. Following hybridization with either of the labeled probes, the blots were washed under high stringency conditions in 0.1× SSPE/1% SDS or 0.1× SSC/1% SDS with equally good results. Blots were then exposed to X-ray film. Upon developing the autoradiographs, similar intensities of the GAPDH hybridization signals in all lanes confirmed uniform RNA loading. Accordingly, relative intensities of the TIG3 bands served as direct indicators of retinoid bioactivity.

Results from the TIG3 Northern hybridization confirmed the low constitutive expression and strong inducibility of this mRNA in psoriatic skin raft cultures. RNA isolated from the culture induced with Tazarotene gave a strong TIG3 mRNA signal at 0.8–0.9 kb, as expected. A band of similar size and slightly greater intensity was observed in the lane corresponding to RNA from the AGN 190299 induced culture. These results indicated that AGN 190299 was strongly bioactive in the TIG3 induction assay. Thus, AGN 190299 was identified as a candidate for therapeutic utility in the treatment of hyperproliferative disorders.

Table 1 summarizes the results of the Northern hybridization procedure. These results confirmed that detection of TIG3 mRNA induction provided a means for identifying a retinoid that affected gene expression in cells exhibiting features of the hyperproliferative disorder associated with the psoriatic phenotype. The TIG3 hybridization probe, used under high stringency conditions, served as an instrument for detecting the TIG3 mRNA in these procedures.

TABLE 1

Hybridization Assay for Retinoid Bioactivity:
TIG3 mRNA Induction in Psoriatic Skin Rafts

|  | Untreated | Tazarotene | AGN 190299 |
|---|---|---|---|
| TIG3 mRNA Expression | (−) | (++) | (++++) |

Assays that detect induced TIG3 mRNA expression as an indicator of retinoid bioactivity can employ a variety of nucleic acid probes based on the sequence of the TIG3 cDNA disclosed herein. In particular, any probe having a polynucleotide sequence that can specifically hybridize the sense strand of the TIG3 cDNA under high stringency conditions is anticipated for use in detecting the TIG3 mRNA in solution or blot hybridization protocols. Further, any set of oligonucleotide primers that can be used to amplify TIG3 polynucleotide sequences starting with a TIG3 mRNA template is also anticipated for use in assays for retinoid bioactivity according to the PCR-based method of our invention.

We particularly note that hybridization probes useful for detecting the TIG3 mRNA need not have a polynucleotide sequence identical to, or perfectly complementary with the polynucleotide sequence given by SEQ ID NO:11. However, hybridization probes useful in connection with the invention must be sufficiently complementary as to be able to hybridize to a mRNA comprising the polynucleotide sequence of SEQ ID NO:11. The lack of requirement for perfect sequence match between the hybridization probe and the TIG3 polynucleotide was demonstrated above by virtue of the established utility of the 0.6 kb amplification product identified by SEQ ID NO:1, a polynucleotide which contained a small number of errors believed to have been introduced during the PCR amplification protocol used to obtain the polynucleotide. In this example, the polynucleotide probe characterized by SEQ ID NO:1 was not identically matched with the sequence of the TIG3 polynucleotide identified by SEQ ID NO:11. Nonetheless, the probe was sufficiently complementary that a single species of TIG3 mRNA was detected by Northern blotting. Accordingly, allelic variants of the TIG3 polynucleotides disclosed herein are also contemplated for use as hybridization probes useful for detecting the TIG3 transcript or cDNA reverse transcribed or amplified using the TIG3 transcript as a template. Those having ordinary skill in the art will appreciate that allelic variants represent sequence variants of genes that are located at similar positions on chromosomes of different individuals. Allelic variants are related structurally, and it is this structural relatedness that renders the variants useful as hybridization probes.

Two different approaches can be used to determine the hybridization characteristics of nucleic acid probes useful in the practice of the present invention. These approaches can be classified as "theoretical" and "empirical." Descriptions of the theoretical and empirical approaches for determining the melting temperatures of nucleic acid probes can be found in *Molecular Cloning: A Laboratory Manual* (Sambrook et al., eds. Cold Spring Harbor Lab Publ. 1989) on pages 11.46 and 11.55, respectively. These methods can be used to identify oligonucleotide primers for use in primer extension and PCR protocols, as well as hybridization probes for use in blotting protocols.

We also contemplate that the aforementioned assay for induction of TIG3 mRNA by retinoids can be adapted for identifying candidate therapeutic agents useful for treating tumors in an individual. As indicated above, certain retinoids are known to be useful for inhibiting the growth of psoriatic plaques (Boehm et al. , *Exp. Opin. Invest. Drugs* 4:593 (1995)) and growth of cells in other hyperproliferative disorders, including some tumors (Nagpal et al. , *Current Pharm. Design* 2:295 (1996)). Clearly, it would be of benefit to identify retinoids having anti-proliferative activity against cells of a tumor biopsy in an in vitro system in advance of commencing drug therapy to inhibit tumor cell proliferation in vivo. More particularly, it would be advantageous to know that a particular retinoid inhibited the growth of cells isolated from a tumor biopsy and cultured in vitro. If a retinoid inhibited cell growth, then that retinoid would be considered as a candidate for administration in vivo for the purpose of inhibiting tumor growth and progression.

Unfortunately, cell proliferation assays do not lend themselves to high throughput drug screening assays. Cell proliferation assays involve numerous steps, including: obtaining a sample of cells representing the hyperproliferative condition, transferring the cells to an in vitro culture, treating a test group of the cells with an agent to be tested for antiproliferative activity, allowing a period of time to pass and assaying the number of living cells at the end of the time period and comparing the number of living cells in the test culture with the number of living cells in a control culture that did not receive the test agent. If there are fewer cells in the culture that received the test agent, when compared with the untreated control sample, then the test agent possessed antiproliferative activity. Conversely, if the test and control cultures contain similar numbers of cells at the end of the time period, then the test agent did not possess antiproliferative activity. Those having ordinary skill in the art will readily appreciate that success of the proliferation assay critically depends on allowing time to pass between the addition of the test agent and the final readout. Methods that reduce the time required to allow for cell proliferation would advantageously accelerate the drug screening assay.

Clearly, it would be advantageous to have available a method for rapidly identifying retinoid compounds useful for inhibiting the growth of cells comprising a patient's tumor. In this way it would be possible to more selectively identify for therapeutic use a retinoid likely to provide therapeutic benefit.

In one embodiment of the invention primary tumor cells are propagated in vitro, administered with a test compound and subsequently assayed for induction of the TIG3 mRNA. Inducibility of the TIG3 mRNA in tumor cells isolated from a biopsy and propagated in vitro provides a useful criterion for identifying retinoids that are candidates for therapeutic use in vivo. This method takes advantage of the unexpected correlation between the inducibility of the TIG3 mRNA following treatment with Tazarotene and the susceptibility of cells to the growth inhibitory activities of the retinoid. In an exemplary procedure described above, Tazarotene inhibited the proliferation of the T47D and ZR75-1 breast cancer cell lines but did not inhibit the proliferation of the MCF-7 and MDA-MB-231 breast cancer cell lines. Significantly, only the T47D and ZR75-1 cell lines were sensitive to the growth-inhibitory activity of retinoids.

Herein we have disclosed the novel TIG3 polynucleotide and uses thereof. The TIG3 mRNA was found to be induced in by RAR-specific retinoids in a variety of skin-derived cells and tissue systems that included primary keratinocyte cultures and normal and psoriatic skin raft cultures. We have also disclosed that the TIG3 mRNA was induced in vivo in biopsy samples of lesional psoriatic skin that had been treated topically with Tazarotene.

In spite of the fact that human keratinocytes express both RARs and RXRs (Fisher et al. , J. Biol. Chem. 269:20629 (1994)), the TIG3 mRNA was induced only by RAR-specific retinoids. Accordingly, the TIG3 polynucleotide was shown to to be an RAR-responsive polynucleotide useful as a marker for the therapeutic efficacy of retinoids in the treatment of hyperproliferative disorders, including psoriasis. Assays for detecting induction of either the TIG3 mRNA or the TIG3 polypeptide will be useful for the systematic identification of candidate compounds useful for treating hyperproliferative disorders such as psoriasis and other diseases.

Contemplated assays for the induction of TIG3 expression can detect the TIG3 mRNA by any of a number of procedures familiar to those having ordinary skill in the art. For example, contemplated assays can detect the TIG3 mRNA by hybridization protocols such as those disclosed by Meinkoth et al. , in *Analytical Biochemistry* 138:267 (1984), the disclosure of which is hereby incorporated by reference. These hybridization protocols include detection of the TIG3 mRNA in a population of immobilized cellular RNA, or alternatively detection of the TIG3 mRNA in a sandwich hybridization protocol. In the latter procedure, an unlabeled probe is affixed to a solid support and serves as a capture probe that hybridizes one region of the TIG3 mRNA. A labeled nucleic acid probe can bind a different region of the TIG3 mRNA in a detection step.

In addition to the hybridization techniques described above, those of ordinary skill in the art will recognize that a large number of other methods of TIG3 mRNA detection will be useful in assays for identifying test compounds for the treatment of hyperproliferative disorders. For example, induction of the TIG3 mRNA can be detected and quantitated by techniques including S1 assays, RNase protection assays and primer extension assays. Those having ordinary skill in the art will be acquainted with the features and utilities of these assays as they relate to RNA detection. General descriptions of these techniques can be found in *Molecular Cloning: A Laboratory Manual* (Sambrook et al. , eds. Cold Spring Harbor Lab Publ. 1989) and *Current Protocols in Molecular Biology* (Ausubel et al. eds. , Greene Publishing Associates and Wiley-Interscience 1987) on pages 7. 58–7.83.

In S1 and RNase protection assays, the TIG3 mRNA is quantitated by hybridizing RNA samples isolated from cells that are uninduced or induced with a retinoid such as Tazarotene with labeled nucleic acid probes harboring sequences complementary to the TIG3 mRNA. If TIG3 mRNA is present in the sample, that mRNA will hybridize to the labeled, complementary nucleic acid strand to form a double-stranded molecule in the region corresponding to the complementary portion of the probe. Those having ordinary skill in the art will appreciate that an exemplary hybridization solution useful for hybridizing mRNA and a labeled probe is an aqueous buffer made 80% formamide. Regions of the probe that are not complementary to the TIG3 mRNA will remain single-stranded. If the probe is a DNA probe, unhybridized probe and single-stranded regions of hybridized probe can be digested with S1 nuclease. If the probe is an RNA probe, unhybridized probe and single-stranded regions of hybridized probe can be digested with RNase. The protected length of the probe, visualized by autoradiography of digest products that have been electrophoretically separated, will be diagnostic of the presence of TIG3 mRNA. When the hybridization procedure is carried out in probe excess, quantitative results can be obtained to indicate the presence of TIG3 mRNA in the starting sample.

In contemplated primer extension assays, an end-labeled oligonucleotide primer which is complementary to a segment of the TIG3 mRNA is hybridized with samples of RNA isolated from cells that are either uninduced or induced with a retinoid such as Tazarotene. If the TIG3 mRNA is present in the sample, the oligonucleotide primer will hybridize to the complementary portion of the TIG3 mRNA. The primer can then be extended to the 5' end of the mRNA by the activity of a reverse transcriptase using the TIG3 mRNA as a template for DNA synthesis. An extension product of the appropriate size, detected on an autoradiograph of electrophoretically separated extension products, will indicate the presence of TIG3 mRNA in the starting population of RNA.

Labels for nucleic acid hybridization probes of the present invention can be any label appropriate for DNA or RNA probes. Such nucleic acid labels can be radioactive or non-radioactive. Non-radioactive labels can be detected by a visible color change or by the emission of light of sufficient intensity that photographic or X-ray film can be exposed.

We also contemplate the use of reporter gene assays to identify retinoids that, like Tazarotene, activate TIG3 gene expression. As used herein, a "reporter gene" is a gene that encodes a "reporter" molecule. A "reporter" can be any molecule that can be detected in cells carrying the corresponding "reporter gene," but not in cells lacking that reporter gene. Thus, for example, a reporter can be an enzyme, a colored or fluorescent product, or an antigen that can be detected by antibodies. Reporter gene assays are ideally suited to study the activity of genes that are regulated at the transcriptional level.

The product of a reporter gene is useful in the study of gene regulation. The protein encoded by a reporter gene can also be employed as a surrogate for detecting the products of a different gene. Accordingly, reporter genes can advantageously serve as indirect indicators of gene activity when the reporter is more easily assayed than the product of the gene of interest. In cases where it is desirable to measure the activity of a weakly expressed gene, or the product of a gene for which an assay is not available, a molecular genetic construct that allows the reporter to be expressed in place of the gene of interest can facilitate such measurements. A protein product is commonly the object of the reporter assay.

Useful reporter molecules may function either as enzymes or as ligands that can be detected by tagged antibodies or other ligand-binding molecules. Specific examples of reporters that are useful in the study of gene regulation include bacterial genes such as those encoding chloramphenicol acetyltransferase (CAT) and beta-galactosidase (β-gal), and the firefly luciferase gene. The protein products of all three of these reporters can easily be detected by means of simple and sensitive enzymatic assays. In addition to reporters that are detected by virtue of their enzymatic activities, other reporters can be detected by antibody-based assays.

The Example presented below illustrates one approach that can be used to obtain genomic clones by a standard library screening protocol. As will be recognized by those having ordinary skill in the art, PCR-based techniques provide an alternative method of isolating the TIG3 promoter.

Example 11 illustrates one technique that can be used to isolate the transcription control region of the TIG3 gene.

EXAMPLE 11

Isolation of the TIG3 Promoter

A nucleic acid segment corresponding to the 5' end of the TIG3 cDNA is first identified for use as a nucleic acid probe according to standard criteria. This polynucleotide is then radiolabeled to high specific activity and used as a hybridization probe to identify recombinant clones harboring the 5' region of the TIG3 cDNA. Some of the genomic clones will also harbor the TIG3 promoter. The transcription initiation site is identified by S1 nuclease mapping or primer extension analysis. The polynucleotide region upstream of the transcription initiation site will possess cis-regulatory elements that confer inducibility of TIG3 downstream sequences by retinoids such as Tazarotene.

A reporter gene construct is prepared by ligating the TIG3 transcription control region upstream of a reporter gene. Plasmid vectors appropriate for this purpose can be commercially obtained. For example, the pGL-BASIC vector (Promega) is a vector that harbors the firefly luciferase coding sequence. This vector would be an appropriate recipient of the TIG3 promoter according to the contemplated method.

With the availability of reporter constructs as described above, it becomes possible to create assays for compounds that induce the TIG3 promoter.

Example 12 illustrates how reporter gene constructs can be used in sensitive assays to identify retinoids that activate the TIG3 promoter.

EXAMPLE 12

Use of TIG3 Reporter Gene Constructs in Assays to Identify Retinoids that Stimulate TIG3 Transcription Stable transfectants harboring the TIG3 promoter/luciferase expression construct of Example 11 are propagated under standard conditions. A culture of the cells is split into four equal parts, and propagated in separate flasks. The first flask is left as an untreated control. A second flask is treated with Tazarotene as a positive control for induction of the expression construct. The third and fourth flasks are treated with test retinoids "A" and "B. " At the end of the treatment period, cells from each of the cultures are harvested and used to prepare cytoplasmic extracts. Luciferase assays are performed using aliquots of each of the four extracts according to standard protocols. The extract from uninduced cells contains a very low level of luciferase activity, while the extract prepared from Tazarotene treated cells has a very high level of activity. These results from the control extracts confirm that Tazarotene induces the TIG3 promoter. The extract of cells induced with retinoid "A" has a level activity similar to the uninduced control extract. This result indicates that retinoid "A" does not exhibit bioactivity in the reporter assay. The extract of cells induced with retinoid "B" has a level of luciferase activity comparable to the Tazarotene treated cell extract. Retinoid "A" exhibits bioactivity in the reporter assay.

In addition to assays based on detection of the TIG3 mRNA or reporter molecules, other assays based on retinoid-dependent cell survival are also contemplated. The approach employed in such assays relies on expression of a selectable marker under transcriptional control of the TIG3 promoter. For example, we contemplate stable cell lines transfected with DNA constructs having the bacterial neomycin drug resistance gene operationally linked to the TIG3 promoter. High level expression of the drug resistance marker will depend on activation of the TIG3 promoter. In the absence of the inducer but in the presence of the drug G418, no cell growth will occur. Conversely, in the presence of an inducer of the TIG3 promoter, high level expression of the neomycin resistance gene will permit cell survival in the presence of G418. Accordingly, retinoids that activate the TIG3 promoter will be identified by virtue of their ability to promote cell survival under drug selection.

Bioactive compounds found to induce TIG3 gene expression will be identified as having potential as therapeutic drugs. The identification of such bioactive compounds can be made according to assays that detect induced expression of the TIG3 mRNA or a reporter gene under transcriptional control of the TIG3 promoter. Alternatively, assays based on induction of the TIG3 protein or on cell survival assays as disclosed above can also be used to identify such compounds. The following Example describes a procedure that can be used to investigate the therapeutic potential of the bioactive compounds, such as AGN 190299.

Example 13 illustrates how bioactive compounds identified according to the methods described herein will be tested for therapeutic value in the treatment of psoriasis. A topical administration protocol is described below.

EXAMPLE 13

Assessing the Therapeutic Potential of Compounds that Stimulate TIG3 Expression A population of adult volunteers having large psoriatic plaques is first identified and then randomly divided into two groups. One group is a control group to be treated with a placebo while the other (test) group is to be treated with a composition containing a bioactive retinoid. The treatment protocol and assessment of drug efficacy is performed essentially as described by Esgleyes-Ribot et al., in the *Journal of the American Academy of Dermatology* 30:581 (1994).

A compound that induces TIG3 gene expression is identified according to methods such as those disclosed above. This compound is then combined into a cream comprising a pharmaceutically acceptable carrier and 0.05% of the bioactive retinoid. The cream is formulated using materials and methods familiar to one having ordinary skill in the art. A placebo consists of the carrier alone and does not contain any retinoid.

Participants in the experimental protocol are appropriately treated either with the placebo or with the cream containing the retinoid to be tested for therapeutic potential. The psoriatic plaques of individuals in the control group are treated with the placebo twice daily for a period of two weeks. Similarly, the psoriatic plaques of individuals in the test group are treated with the composition containing bioactive retinoid twice daily for the same period.

Individuals administered with the bioactive retinoid show clinical improvement after the first two weeks of treatment. In this context, clinical improvement is assessed by erythema, induration and scaling. Immunohistochemical analysis of standard markers indicates that normalization of skin histology parallels the clinical improvement observed in lesions treated with the composition containing the bioactive retinoid. Similarly, expression of inflammatory markers is reduced in biopsies obtained from lesions treated with the composition containing the bioactive retinoid. Few if any members of the control group show clinical improvement. These findings indicate the bioactive retinoid is effective as a psoriasis treatment, and that treatment of psoriatic lesions with the placebo alone had no beneficial effect.

What is claimed is:

1. A method of identifying a compound for treatment of a hyperproliferative disorder of skin, comprising the steps:
    a. obtaining a control sample containing RNA from an untreated control culture of skin cells;
    b. obtaining a sample containing RNA from a test culture of said skin cells, wherein said test culture has been treated with a test compound;
    c. quantitating the amount of Tazarotene Inducible Gene-3 (TIG3) RNA present in each of said samples, said TIG3 RNA encoding a polypeptide sequence comprising SEQ ID NO:12;
    d. comparing the amount of TIG3 RNA in each of said samples to determine if the amount of TIG3 RNA in said test sample is greater or lesser than the amount of TIG3 RNA in said control sample, wherein said test compound is identified as a compound for the treatment of the hyperproliferative disorder if the amount of TIG3 RNA in said test sample is greater than the amount of TIG3 RNA in said control sample.

2. The method of claim 1 wherein said TIG3 RNA has a polynucleotide sequence comprising SEQ ID NO:11, wherein U's are substituted for T's.

3. The method of either of claims 1 or 2, wherein step c, comprises:
    (i) hybridizing RNA from said control sample and said test sample to a probe having a sufficient number of consecutive nucleotides complementary to said TIG3 mRNA to specifically hybridize with said TIG3 mRNA under hybridization conditions wherein said probe will not hybridize with non-TIG3 nucleic acids; and
    (ii) quantitating the amount of hybridization between said probe and nucleic acids from each of said control sample and said test sample.

4. The method of claim 1, wherein the control culture comprises keratinocytes or fibroblasts.

5. The method of claim 3, wherein said probe is labeled with a radioactive label.

6. The method of claim 3, wherein step (ii) comprises autoradiography.

7. The method of claim 3, wherein the RNA contained in said control sample and the RNA contained in said test sample are immobilized to a solid support.

8. The method of either of claims 1 or 2, wherein step c, comprises:
    (i) amplifying mRNA present in each of said samples, to produce a TIG3-specific amplification product; and
    (ii) quantitating TIG3-specific amplification products produced when control and test samples are used as sources of mRNA for the amplification step.

9. The method of claim 8, further comprising comparing the results of step (ii) to the amount of a constitutively expressed mRNA present in both said negative control sample and said test sample.

10. The method of claim 8, wherein said TIG3-specific amplification products are produced using at least one primer comprising a sequence selected from the group consisting of SEQ ID NO:13 and SEQ ID NO:14 .

11. The method of claim 1, wherein step c, comprises a nuclease protection assay.

12. The method of either of claims 11 or 2, comprising the steps:
    a. hybridizing with nucleic acids from said control sample and said test sample a single stranded polynucleotide probe, said probe comprising a sequence able to hybridize specifically to TIG3 mRNA or cDNA under hybridizing conditions wherein said probe will not hybridize to non-TIG3 nucleic acids;
    b. digesting products of hybridizing step (a) with a single-strand-specific nuclease; and
    c. quantitating the amount of undigested probe remaining after step b, as an indication of the amount of TIG3 RNA in each said control and test cultures.

13. The method of either of claims 1 or 2, wherein the skin cells of steps (a) and (b) are from psoriatic tissue.

14. The method of either of claims 1 or 2, wherein the skin cells of steps (a) and (b) are from non-psoriatic tissue.

15. The method of claim 12, wherein said enzyme is S1 nuclease or RNase.

16. The method of either of claims 1 or 2, wherein step c. comprises:

(i) hybridizing with nucleic acids from said control sample and said test sample a labeled primer able to hybridize specifically to TIG3 RNA under hybridizing conditions wherein said probe will not hybridize to non-TIG3 nucleic acids;

(ii) extending the primer hybridized in step (i) by the activity of a reverse transcriptase enzyme to produce a TIG3-specific, labeled cDNA;

(iii) quantitating the amount of labeled cDNA produced in step (ii) as an indication of the presence of TIG3 RNA.

17. The method of claim 16, wherein the primer is labeled at its 5' end.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 588 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Other
        ( B ) LOCATION: 1...588
        ( D ) OTHER INFORMATION: Polynucleotide sequence of pTA-TIG3 insert ( x i ) SEQUENCE DESCRIPTION: SEQ ID NO:1:

```
TGAGTACCCC  GGGGCTGGCT  CCTCCGGTGT  CTTCTCAGTC  CTGAGCAACA  GTGCAGAGGT     60

GAAACGGGGG  CGCCTGGAAG  ATGTGGTGGG  AGGCTGTTGC  TATCGGGTCA  ACAACAGCTT    120

GGACCATGAG  TACCAACCAC  GGCCCGTGGA  GGTGATCATC  AGTTCCGCGA  AGGAGATGGT    180

TGGTCAGAAG  ATGAAGTACA  GTATTGTGAG  CAGGAACTGT  GAGCACTTTG  TCGCCCAGCT    240

GAGATATGGC  AAGTCCCGCT  GTAAACAGGT  GGAAAAGGCC  AAGGTTGAAG  TCGGTGTCGC    300

CACGGCGCTT  GGAATCCTGG  TTGTTGCTGG  ATGCTCTTTT  GCGATTAGGA  GATACCAAAA    360

AAAAGCAACA  GCCTGAAGCA  GCCACAAAAT  CCTGTGTTAG  AAGCAGCTGT  GGGGGTCCCA    420

GTGGAGATGA  GCCTCCCCCA  TGCCTCCAGC  AGCCTGACCC  TCGTGCCCTG  TCTCAGGCGT    480

TCTCTAGATC  CTTTCCTCTG  TTTCCCTCTC  TCGCTGGCAA  AAGTATGATC  TAATTGAAAC    540

AAGACTGAAG  GATCAATAAA  CAGCCATCTG  CCCCTTCAAA  AAAAAAA                  588
```

( 2 ) INFORMATION FOR SEQ ID NO:2:

( i ) SEQUENCE CHARACTERISTICS:
    ( A ) LENGTH: 588 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: Coding Sequence
    ( B ) LOCATION: 2...373
    ( D ) OTHER INFORMATION: Consensus sequence derived
         from six clonal isolates ( x i ) SEQUENCE DESCRIPTION: SEQ ID NO:2:

```
T  GAG  TAC  CCC  GGG  GCT  GGC  TCC  TCC  GGT  GTC  TTC  TCA  GTC  CTG  AGC  AAC       49
   Glu  Tyr  Pro  Gly  Ala  Gly  Ser  Ser  Gly  Val  Phe  Ser  Val  Leu  Ser  Asn
   1              5                        10                       15

AGT  GCA  GAG  GTG  AAA  CGG  GAG  CGC  CTG  GAA  GAT  GTG  GTG  GGA  GGC  TGT          97
Ser  Ala  Glu  Val  Lys  Arg  Glu  Arg  Leu  Glu  Asp  Val  Val  Gly  Gly  Cys
              20                       25                       30

TGC  TAT  CGG  GTC  AAC  AAC  AGC  TTG  GAC  CAT  GAG  TAC  CAA  CCA  CGG  CCC         145
Cys  Tyr  Arg  Val  Asn  Asn  Ser  Leu  Asp  His  Glu  Tyr  Gln  Pro  Arg  Pro
          35                       40                       45

GTG  GAG  GTG  ATC  ATC  AGT  TCT  GCG  AAG  GAG  ATG  GTT  GGT  CAG  AAG  ATG         193
Val  Glu  Val  Ile  Ile  Ser  Ser  Ala  Lys  Glu  Met  Val  Gly  Gln  Lys  Met
     50                       55                       60

AAG  TAC  AGT  ATT  GTG  AGC  AGG  AAC  TGT  GAG  CAC  TTT  GTC  ACC  CAG  CTG         241
Lys  Tyr  Ser  Ile  Val  Ser  Arg  Asn  Cys  Glu  His  Phe  Val  Thr  Gln  Leu
65                       70                       75                       80

AGA  TAT  GGC  AAG  TCC  CGC  TGT  AAA  CAG  GTG  GAA  AAG  GCC  AAG  GTT  GAA         289
Arg  Tyr  Gly  Lys  Ser  Arg  Cys  Lys  Gln  Val  Glu  Lys  Ala  Lys  Val  Glu
                    85                       90                       95

GTC  GGT  GTC  GCC  ACG  GCG  CTT  GGA  ATC  CTG  GTT  GTT  GCT  GGA  TGC  TCT         337
Val  Gly  Val  Ala  Thr  Ala  Leu  Gly  Ile  Leu  Val  Val  Ala  Gly  Cys  Ser
               100                      105                      110

TTT  GCG  ATT  AGG  AGA  TAC  CAA  AAA  AAA  GCA  ACA  GCC  TGAAGCAGCC  ACAAAA         389
Phe  Ala  Ile  Arg  Arg  Tyr  Gln  Lys  Lys  Ala  Thr  Ala
               115                      120

TCCTGTGTTA  GAAGCAGCTG  TGGGGGTCCC  AGTGGAGATG  AGCCTCCCCC  ATGCCTCCAG               449

CAGCCTGACC  CTCGTGCCCT  GTCTCAGGCG  TTCTCTAGAT  CCTTTCCTCT  GTTTCCCTCT               509

CTCGCTGGCA  AAAGTATGAT  CTAATTGAAA  CAAGACTGAA  GGATCAATAA  ACAGCCATCT               569

GCCCCTTCAA  AAAAAAAA                                                                 588
```

( 2 ) INFORMATION FOR SEQ ID NO:3:

( i ) SEQUENCE CHARACTERISTICS:
    ( A ) LENGTH: 124 amino acids
    ( B ) TYPE: amino acid
    ( C ) STRANDEDNESS: single
    ( D ) TOPOLOGY: linear ( i i ) MOLECULE TYPE: protein ( v ) FRAGMENT TYPE: internal ( x i ) SEQUENCE DESCRIPTION: SEQ ID NO:3:

```
Glu  Tyr  Pro  Gly  Ala  Gly  Ser  Ser  Gly  Val  Phe  Ser  Val  Leu  Ser  Asn
1              5                        10                       15

Ser  Ala  Glu  Val  Lys  Arg  Glu  Arg  Leu  Glu  Asp  Val  Val  Gly  Gly  Cys
              20                       25                       30

Cys  Tyr  Arg  Val  Asn  Asn  Ser  Leu  Asp  His  Glu  Tyr  Gln  Pro  Arg  Pro
```

|     | 35 |     |     |     |     | 40 |     |     |     |     | 45 |     |     |     |
|-----|-----|-----|-----|-----|-----|-----|-----|-----|-----|-----|-----|-----|-----|-----|
| Val | Glu | Val | Ile | Ile | Ser | Ser | Ala | Lys | Glu | Met | Val | Gly | Gln | Lys | Met |
|     | 50  |     |     |     |     | 55  |     |     |     |     | 60  |     |     |     |

Val Glu Val Ile Ile Ser Ser Ala Lys Glu Met Val Gly Gln Lys Met
    50                      55                      60

Lys Tyr Ser Ile Val Ser Arg Asn Cys Glu His Phe Val Thr Gln Leu
65                      70                  75                  80

Arg Tyr Gly Lys Ser Arg Cys Lys Gln Val Glu Lys Ala Lys Val Glu
                85                  90                  95

Val Gly Val Ala Thr Ala Leu Gly Ile Leu Val Val Ala Gly Cys Ser
            100                 105                 110

Phe Ala Ile Arg Arg Tyr Gln Lys Lys Ala Thr Ala
            115             120

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

( x i ) SEQUENCE DESCRIPTION: SEQ ID NO:4:

TTCACCTCTG CACTGTTGCT C                                             21

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

ATTTAGGTGA CACTATAGAA GAGC                                     24

( 2 ) INFORMATION FOR SEQ ID NO:6:

( i ) SEQUENCE CHARACTERISTICS:
        ( A ) LENGTH: 207 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

GGAGCACCAG ACCTCCTCTT GGCTTCGAGA TGGCTTCGCC ACACCAAGAG CCCAAACCTG     60

GAGACCTGAT TGAGATTTTC CGCCTTGGCT ATGAGCACTG GGCCCTGTAT ATAGGAGATG    120

GCTACGTGAT CCATCTGGCT CCTCCAAGTG AGTACCCCGG GGCTGGCTCC TCCAGTGTCT    180

TCTCAGTCCT GAGCAACAGT GCAGAGG                                                         207

( 2 ) INFORMATION FOR SEQ ID NO:7:

( i ) SEQUENCE CHARACTERISTICS:
        ( A ) LENGTH: 736 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
  ( A ) NAME/KEY: Coding Sequence
  ( B ) LOCATION: 30...521
  ( D ) OTHER INFORMATION:

( x i ) SEQUENCE DESCRIPTION: SEQ ID NO:7:

```
GGAGCACCAG ACCTCCTCTT GGCTTCGAG ATG GCT TCG CCA CAC CAA GAG CCC         53
                                   Met Ala Ser Pro His Gln Glu Pro
                                    1               5

AAA CCT GGA GAC CTG ATT GAG ATT TTC CGC CTT GGC TAT GAG CAC TGG        101
Lys Pro Gly Asp Leu Ile Glu Ile Phe Arg Leu Gly Tyr Glu His Trp
     10              15                  20

GCC CTG TAT ATA GGA GAT GGC TAC GTG ATC CAT CTG GCT CCT CCA AGT        149
Ala Leu Tyr Ile Gly Asp Gly Tyr Val Ile His Leu Ala Pro Pro Ser
 25              30                  35                      40

GAG TAC CCC GGG GCT GGC TCC TCC GGT GTC TTC TCA GTC CTG AGC AAC        197
Glu Tyr Pro Gly Ala Gly Ser Ser Gly Val Phe Ser Val Leu Ser Asn
                 45                  50                  55

AGT GCA GAG GTG AAA CGG GGG CGC CTG GAA GAT GTG GTG GGA GGC TGT        245
Ser Ala Glu Val Lys Arg Gly Arg Leu Glu Asp Val Val Gly Gly Cys
             60                  65                  70

TGC TAT CGG GTC AAC AAC AGC TTG GAC CAT GAG TAC CAA CCA CGG CCC        293
Cys Tyr Arg Val Asn Asn Ser Leu Asp His Glu Tyr Gln Pro Arg Pro
         75                  80                  85

GTG GAG GTG ATC ATC AGT TCT GCG AAG GAG ATG GTT GGT CAG AAG ATG        341
Val Glu Val Ile Ile Ser Ser Ala Lys Glu Met Val Gly Gln Lys Met
     90                  95                 100

AAG TAC AGT ATT GTG AGC AGG AAC TGT GAG CAC TTT GTC ACC CAG CTG        389
Lys Tyr Ser Ile Val Ser Arg Asn Cys Glu His Phe Val Thr Gln Leu
105              110                 115                     120

AGA TAT GGC AAG TCC CGC TGT AAA CAG GTG GAA AAG GCC AAG GTT GAA        437
Arg Tyr Gly Lys Ser Arg Cys Lys Gln Val Glu Lys Ala Lys Val Glu
                 125                 130                     135

GTC GGT GTG GCC ACG GCG CTT GGA ATC CTG GTT GTT GCT GGA TGC TCT        485
Val Gly Val Ala Thr Ala Leu Gly Ile Leu Val Val Ala Gly Cys Ser
                 140             145                     150

TTT GCG ATT AGG AGA TAC CAA AAA AAA GCA ACA GCC TGAAGCAGCC ACAAAA      537
Phe Ala Ile Arg Arg Tyr Gln Lys Lys Ala Thr Ala
         155                 160

TCCTGTGTTA GAAGCAGCTG TGGGGGTCCC AGTGGAGATG AGCCTCCCCC ATGCCTCCAG      597

CAGCCTGACC CTCGTGCCCT GTCTCAGGCG TTCTCTAGAT CCTTTCCTCT GTTTCCCTCT      657

CTCGCTGGCA AAAGTATGAT CTAATTGAAA CAAGACTGAA GGATCAATAA ACAGCCATCT      717

GCCCCTTCAA AAAAAAAA                                                   736
```

( 2 ) INFORMATION FOR SEQ ID NO:8:

( i ) SEQUENCE CHARACTERISTICS:
    ( A ) LENGTH: 164 amino acids
    ( B ) TYPE: amino acid
    ( C ) STRANDEDNESS: single
    ( D ) TOPOLOGY: linear ( i i ) MOLECULE TYPE: protein ( v ) FRAGMENT TYPE: internal ( x i ) SEQUENCE DESCRIPTION: SEQ ID NO:8:

```
Met Ala Ser Pro His Gln Glu Pro Lys Pro Gly Asp Leu Ile Glu Ile
 1               5                  10                  15

Phe Arg Leu Gly Tyr Glu His Trp Ala Leu Tyr Ile Gly Asp Gly Tyr
             20                  25                  30
```

| | | | | | | | | | | | | | | |
|---|---|---|---|---|---|---|---|---|---|---|---|---|---|---|
|Val|Ile|His|Leu|Ala|Pro|Pro|Ser|Glu|Tyr|Pro|Gly|Ala|Gly|Ser|Ser|
| | |35| | | | |40| | | | |45| | | |

| | | | | | | | | | | | | | | | |
|---|---|---|---|---|---|---|---|---|---|---|---|---|---|---|---|
|Gly|Val|Phe|Ser|Val|Leu|Ser|Asn|Ser|Ala|Glu|Val|Lys|Arg|Gly|Arg|
| |50| | | | |55| | | | |60| | | | |

| | | | | | | | | | | | | | | | |
|---|---|---|---|---|---|---|---|---|---|---|---|---|---|---|---|
|Leu|Glu|Asp|Val|Val|Gly|Gly|Cys|Cys|Tyr|Arg|Val|Asn|Asn|Ser|Leu|
|65| | | | |70| | | | |75| | | | |80|

| | | | | | | | | | | | | | | | |
|---|---|---|---|---|---|---|---|---|---|---|---|---|---|---|---|
|Asp|His|Glu|Tyr|Gln|Pro|Arg|Pro|Val|Glu|Val|Ile|Ile|Ser|Ser|Ala|
| | | | |85| | | | |90| | | | |95| |

| | | | | | | | | | | | | | | | |
|---|---|---|---|---|---|---|---|---|---|---|---|---|---|---|---|
|Lys|Glu|Met|Val|Gly|Gln|Lys|Met|Lys|Tyr|Ser|Ile|Val|Ser|Arg|Asn|
| | | |100| | | | |105| | | | |110| | |

| | | | | | | | | | | | | | | | |
|---|---|---|---|---|---|---|---|---|---|---|---|---|---|---|---|
|Cys|Glu|His|Phe|Val|Thr|Gln|Leu|Arg|Tyr|Gly|Lys|Ser|Arg|Cys|Lys|
| | |115| | | | |120| | | | |125| | | |

| | | | | | | | | | | | | | | | |
|---|---|---|---|---|---|---|---|---|---|---|---|---|---|---|---|
|Gln|Val|Glu|Lys|Ala|Lys|Val|Glu|Val|Gly|Val|Ala|Thr|Ala|Leu|Gly|
| |130| | | | |135| | | | |140| | | | |

| | | | | | | | | | | | | | | | |
|---|---|---|---|---|---|---|---|---|---|---|---|---|---|---|---|
|Ile|Leu|Val|Val|Ala|Gly|Cys|Ser|Phe|Ala|Ile|Arg|Arg|Tyr|Gln|Lys|
|145| | | | |150| | | | |155| | | | |160|

Lys Ala Thr Ala (2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TTGGATCCTG TGGCTGCTTC AGGCTGTTGC        30

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TCAAGCTTCC ACCATGGCTT CGCCACACCA AGAGCCCA        38

(2) INFORMATION FOR SEQ ID NO:11:

(i) SEQUENCE CHARACTERISTICS:
        (A) LENGTH: 505 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 1...492
        (D) OTHER INFORMATION:

(xi) SEQUENCE DESCRIPTION: SEQ ID NO:11:

| | | | | | | | | | | | | | | | |
|---|---|---|---|---|---|---|---|---|---|---|---|---|---|---|---|
|ATG|GCT|TCG|CCA|CAC|CAA|GAG|CCC|AAA|CCT|GGA|GAC|CTG|ATT|GAG|ATT|
|Met|Ala|Ser|Pro|His|Gln|Glu|Pro|Lys|Pro|Gly|Asp|Leu|Ile|Glu|Ile|
|1| | | |5| | | | |10| | | | |15| |

48

| | | | | | | | | | | | | | | | |
|---|---|---|---|---|---|---|---|---|---|---|---|---|---|---|---|
|TTC|CGC|CTT|GGC|TAT|GAG|CAC|TGG|GCC|CTG|TAT|ATA|GGA|GAT|GGC|TAC|

96

|  |  |  |  |  |  |  |  |  |  |  |  |  |  |  |  |
|---|---|---|---|---|---|---|---|---|---|---|---|---|---|---|---|
| Phe | Arg | Leu | Gly<br>20 | Tyr | Glu | His | Trp | Ala<br>25 | Leu | Tyr | Ile | Gly | Asp<br>30 | Gly | Tyr |

| GTG | ATC | CAT | CTG | GCT | CCT | CCA | AGT | GAG | TAC | CCC | GGG | GCT | GGC | TCC | TCC | 144 |
|---|---|---|---|---|---|---|---|---|---|---|---|---|---|---|---|---|
| Val | Ile | His<br>35 | Leu | Ala | Pro | Pro | Ser<br>40 | Glu | Tyr | Pro | Gly | Ala<br>45 | Gly | Ser | Ser | |

| AGT | GTC | TTC | TCA | GTC | CTG | AGC | AAC | AGT | GCA | GAG | GTG | AAA | CGG | GGG | CGC | 192 |
|---|---|---|---|---|---|---|---|---|---|---|---|---|---|---|---|---|
| Ser | Val<br>50 | Phe | Ser | Val | Leu | Ser<br>55 | Asn | Ser | Ala | Glu | Val<br>60 | Lys | Arg | Gly | Arg | |

| CTG | GAA | GAT | GTG | GTG | GGA | GGC | TGT | TGC | TAT | CGG | GTC | AAC | AAC | AGC | TTG | 240 |
|---|---|---|---|---|---|---|---|---|---|---|---|---|---|---|---|---|
| Leu<br>65 | Glu | Asp | Val | Val | Gly<br>70 | Gly | Cys | Cys | Tyr | Arg<br>75 | Val | Asn | Asn | Ser | Leu<br>80 | |

| GAC | CAT | GAG | TAC | CAA | CCA | CGG | CCC | GTG | GAG | GTG | ATC | ATC | AGT | TCT | GCG | 288 |
|---|---|---|---|---|---|---|---|---|---|---|---|---|---|---|---|---|
| Asp | His | Glu | Tyr | Gln<br>85 | Pro | Arg | Pro | Val | Glu<br>90 | Val | Ile | Ile | Ser | Ser<br>95 | Ala | |

| AAG | GAG | ATG | GTT | GGT | CAG | AAG | ATG | AAG | TAC | AGT | ATT | GTG | AGC | AGG | AAC | 336 |
|---|---|---|---|---|---|---|---|---|---|---|---|---|---|---|---|---|
| Lys | Glu | Met | Val<br>100 | Gly | Gln | Lys | Met | Lys<br>105 | Tyr | Ser | Ile | Val | Ser<br>110 | Arg | Asn | |

| TGT | GAG | CAC | TTT | GTC | GCC | CAG | CTG | AGA | TAT | GGC | AAG | TCC | CGC | TGT | AAA | 384 |
|---|---|---|---|---|---|---|---|---|---|---|---|---|---|---|---|---|
| Cys | Glu | His<br>115 | Phe | Val | Ala | Gln | Leu<br>120 | Arg | Tyr | Gly | Lys | Ser<br>125 | Arg | Cys | Lys | |

| CAG | GTG | GAA | AAG | GCC | AAG | GTT | GAA | GTC | GGT | GTG | GCC | ACG | GCG | CTT | GGA | 432 |
|---|---|---|---|---|---|---|---|---|---|---|---|---|---|---|---|---|
| Gln | Val<br>130 | Glu | Lys | Ala | Lys<br>135 | Val | Glu | Val | Gly | Val<br>140 | Ala | Thr | Ala | Leu | Gly | |

| ATC | CTG | GTT | GTT | GCT | GGA | TGC | TCT | TTT | GCG | ATT | AGG | AGA | TAC | CAA | AAA | 480 |
|---|---|---|---|---|---|---|---|---|---|---|---|---|---|---|---|---|
| Ile | Leu | Val | Val<br>145 | Ala | Gly | Cys<br>150 | Ser | Phe | Ala | Ile<br>155 | Arg | Arg | Tyr | Gln | Lys<br>160 | |

| AAA | GCA | ACA | GCC | TGAAGCAGCC | ACA | | | | | | | | | | | 505 |
|---|---|---|---|---|---|---|---|---|---|---|---|---|---|---|---|---|
| Lys | Ala | Thr | Ala | | | | | | | | | | | | | |

(2) INFORMATION FOR SEQ ID NO:12:

(i) SEQUENCE CHARACTERISTICS:
        (A) LENGTH: 164 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:12:

| Met<br>1 | Ala | Ser | Pro | His<br>5 | Gln | Glu | Pro | Lys | Pro<br>10 | Gly | Asp | Leu | Ile | Glu<br>15 | Ile |
|---|---|---|---|---|---|---|---|---|---|---|---|---|---|---|---|
| Phe | Arg | Leu | Gly<br>20 | Tyr | Glu | His | Trp | Ala<br>25 | Leu | Tyr | Ile | Gly | Asp<br>30 | Gly | Tyr |
| Val | Ile | His<br>35 | Leu | Ala | Pro | Pro | Ser<br>40 | Glu | Tyr | Pro | Gly | Ala<br>45 | Gly | Ser | Ser |
| Ser | Val<br>50 | Phe | Ser | Val | Leu | Ser<br>55 | Asn | Ser | Ala | Glu | Val<br>60 | Lys | Arg | Gly | Arg |
| Leu<br>65 | Glu | Asp | Val | Val | Gly<br>70 | Gly | Cys | Cys | Tyr | Arg<br>75 | Val | Asn | Asn | Ser | Leu<br>80 |
| Asp | His | Glu | Tyr | Gln<br>85 | Pro | Arg | Pro | Val | Glu<br>90 | Val | Ile | Ile | Ser | Ser<br>95 | Ala |
| Lys | Glu | Met | Val<br>100 | Gly | Gln | Lys | Met | Lys<br>105 | Tyr | Ser | Ile | Val | Ser<br>110 | Arg | Asn |
| Cys | Glu | His<br>115 | Phe | Val | Ala | Gln | Leu<br>120 | Arg | Tyr | Gly | Lys | Ser<br>125 | Arg | Cys | Lys |
| Gln | Val<br>130 | Glu | Lys | Ala | Lys<br>135 | Val | Glu | Val | Gly | Val<br>140 | Ala | Thr | Ala | Leu | Gly |

```
Ile  Leu  Val  Val  Ala  Gly  Cys  Ser  Phe  Ala  Ile  Arg  Arg  Tyr  Gln  Lys
145                      150                      155                      160

Lys  Ala  Thr  Ala
```

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GCGACAGCCT GAAGCAGC        18

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TTATTGATCC TTCAGTCTTG        20